United States Patent
Zhang et al.

(10) Patent No.: US 11,039,784 B2
(45) Date of Patent: Jun. 22, 2021

(54) SLEEP PROFILING SYSTEM WITH FEATURE GENERATION AND AUTO-MAPPING

(71) Applicant: AGENCY FOR SCIENCE, TECHNOLOGY AND RESEARCH, Singapore (SG)

(72) Inventors: Zhuo Zhang, Singapore (SG); Cuntai Guan, Singapore (SG); Hai Hong Zhang, Singapore (SG); Huijuan Yang, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 663 days.

(21) Appl. No.: 15/533,372

(22) PCT Filed: Dec. 7, 2015

(86) PCT No.: PCT/SG2015/050488
§ 371 (c)(1),
(2) Date: Jun. 5, 2017

(87) PCT Pub. No.: WO2016/089313
PCT Pub. Date: Jun. 9, 2016

(65) Prior Publication Data
US 2017/0360362 A1    Dec. 21, 2017

(30) Foreign Application Priority Data
Dec. 5, 2014 (SG) .......................... 10201408145X

(51) Int. Cl.
*A61B 5/00* (2006.01)
*A61B 5/372* (2021.01)
(Continued)

(52) U.S. Cl.
CPC ............ *A61B 5/4812* (2013.01); *A61B 5/316* (2021.01); *A61B 5/369* (2021.01); *A61B 5/7264* (2013.01); *A61B 5/7267* (2013.01)

(58) Field of Classification Search
None
See application file for complete search history.

(56) References Cited

U.S. PATENT DOCUMENTS

2008/0154111 A1*  6/2008  Wu ................... A61B 5/0478
                                                        600/383
2008/0195166 A1   8/2008  Sun et al.
(Continued)

FOREIGN PATENT DOCUMENTS

KR   10-2012-0108491 A   10/2012
KR        10-1349751 B1    2/2014
(Continued)

OTHER PUBLICATIONS

Katayama et al. Staging of Awake and Sleep Based on Feature Map. Systems and Computers in Japan, vol. 26, No. 7, 1995. (Year: 1995).*

(Continued)

*Primary Examiner* — Etsub D Berhanu
(74) *Attorney, Agent, or Firm* — Womble Bond Dickinson (US) LLP

(57) ABSTRACT

A method for profiling sleep of an individual is provided. The method includes defining a sleep feature space for the individual, measuring a brain wave for the individual during the individual's sleep, and mapping the sleep feature space in response to a comparison of the brain wave and a previous brain wave measurement used to define the sleep feature space. The brain wave may comprise a brain wave spectrum. The sleep feature space may comprise, or be composed of, spectral power and envelope measures. The method also includes modelling the mapped sleep feature space in (Continued)

response to recognized neural network patterns corresponding to each of a plurality of sleep stages derived from recognizing the neural network patterns from the sleep feature space and deriving a sleep profile for the individual from sleep stages determined in response to the modelled mapped sleep feature space and the brain wave of the individual.

7 Claims, 8 Drawing Sheets

(51) Int. Cl.
    *A61B 5/316*     (2021.01)
    *A61B 5/369*     (2021.01)

(56) References Cited

U.S. PATENT DOCUMENTS

| | | |
|---|---|---|
| 2009/0192556 A1 | 7/2009 | Wu et al. |
| 2014/0221779 A1 | 8/2014 | Schoonover et al. |
| 2014/0275829 A1* | 9/2014 | Berezhnyy ............ A61B 5/0478 600/301 |
| 2015/0038804 A1* | 2/2015 | Younes .............. A61B 5/04012 600/301 |

FOREIGN PATENT DOCUMENTS

| | | |
|---|---|---|
| WO | WO 2014/175684 A1 | 10/2014 |
| WO | WO 2014/200433 A1 | 12/2014 |

OTHER PUBLICATIONS

Shumway R.H. & Stoffer D.S., Chapter 7: Statistical Methods in the Frequency Domain, *Time Series Analysis and Its Applications: with R Examples*—(Third Edition), Dec. 31, 2011, Book cover, title pages, table of contents and pp. 405-506.

IP Office of Singapore, Notification of Transmittal of International Search Report and Written Opinion, or the Declaration for counterpart International Application No. PCT/SG2015/040488, dated Feb. 2, 2016, 13 pages.

Barcaro U. et al., Quantitative description of EEG periodicities during stationary sleep stages. *Journal of Sleep Research*, Dec. 31, 1994, vol. 3, No. 4, pp. 214-222.

PCT International Preliminary Report on Patentability for PCT/SG2015/050488, dated Jun. 15, 2017, 10 pages.

\* cited by examiner

SLEEP PROFILING SYSTEM WITH FEATURE GENERATION AND AUTO-MAPPING

CROSS-REFERENCE TO RELATED APPLICATIONS

This patent application is a U.S. National Phase application under 35 U.S.C. § 371 of International Application No. PCT/SG2015/050488, filed on Dec. 7, 2015, entitled SLEEP PROFILING SYSTEM WITH FEATURE GENERATION AND AUTO-MAPPING, which claims priority from Singapore Patent Application No. 10201408145X, filed on Dec. 5, 2014.

FIELD OF THE INVENTION

The present invention relates to the sleep profiling. In particular, it relates to an approach for sleep profiling using auto-mapping and generation of computationally efficient, representative features to provide a robust platform for, for example, home-based sleep monitoring.

BACKGROUND

Sleep plays an important role in a person's overall health and well-being. Research has shown that good sleep keeps a person's heart healthier, reduces stress and inflammation, bolsters memory, and even prevents cancer. In 2007, the American Academy of Sleep Medicine (AASM) developed a new guideline of terminology and scoring rules for sleep-related phenomena based on the R&K score named after the key developers, Allan Rechtschaffen and Anthony Kales. According to the AASM, the different stages of a sleep cycle include rapid eye movement (REM) sleep (stage R, corresponding to REM in R&K rule) and non-rapid eye movement sleep (NREM). NREM sleep can be further classified into stages N1, N2 and N3 (corresponding to S1, S2 and S3+S4 of R&K rule respectively). N3 is also called slow wave sleep (SWS) and is the deepest stage of sleep. All sleep stages and awakened states 106, 108, 110, 112, 114, 116 can be determined and displayed on a hypnogram, a form of polysomnography that represents the stages of sleep 102 as a function of time 104, as shown in FIG. 1.

Traditionally, sleep monitoring was only conducted in professional sleep labs, using polysomnographic (PSG) equipment recording electroencephalogram (EEG), electrooculograms (EOG) and elecromyograms (EMGs). With the recordings from multiple sensors a trained specialist manually annotates the sleep stages according to the AASM scoring system. The high cost of such a setup has restricted the applications of sleep research. In recent years, however, the development of light-weight EEG sensors, e.g., EEG headbands has made home-based sleep monitoring systems possible. The method of automatic sleep scoring (staging) based on a single EEG channel plays an essential role in such systems.

The manual sleep scoring process is based on 30-second sequential epochs. The sleep specialist measures the frequency and amplitude of waveforms and applies standard criteria for scoring sleep stages. There are several rules to be followed: 1) EEG readings take precedence over EOG & EMG data; 2) Sleep architecture has to be taken into consideration; 3) Majority rule is to be applied when 2 or more stages co-exist during a single epoch; and 4) Patient specific factors are to be taken into consideration during the scoring process. Developing methods to automate the sleep staging process needs to take into consideration the above factors/rules.

Though a number of features can be extracted from EEG signals for sleep staging, some show little correlation with sleep stages while others are redundant. Yet more require high order computational power that prevents real-time processing. A set of computationally efficient, representative features for accurate sleep stage detection have not yet been proposed. Furthermore, the sleep hyponogram as a tool for professionals to analyse sleep patterns gives less-intuitive information for the lay person to understand his or her sleep profile.

Various approaches have been reported on automatic sleep staging based on EEG data from a single channel. One approach detected the arousal states of humans through the mean frequency feature of a single EEG for autoregressive Hidden Markov Models (HMM), with the approach achieving a wake-drowsiness detection rate of 70%. Another employed the use of more features, including spectral entropy, autoregressive parameters, and complexity stochastic measurements to build a HMM model for sleep staging. This approach worked for predicting sleep stages N3 and N4 but was not able to distinguish accurately between wake, N1 and N2 stages. A third approach taught using EEG modelling by the application of Kalman filter and HMM, and the agreement rate in the testing set was reported to be 60.14%. A final approach proposed a Gaussian Observation HMM to detect sleep stages, and achieved an overall agreement of 74.6%, with an accuracy of 86% for Wake but only 22% for stage N1. A report evaluated the sleep staging accuracy of a home sleep scoring system and discovered that the system displayed large deviation from the standard measure, especially in the wake-to-N1 transition stage and concluded that reliable home based sleep scoring systems are yet to arrive.

Accordingly, what is needed is a more intuitive and information-enriched sleep profiling methodology for home-based sleep monitoring systems. Furthermore, other desirable features and characteristics will become apparent from the subsequent detailed description, taken in conjunction with the accompanying drawings and this background of the disclosure.

SUMMARY OF THE INVENTION

In accordance with the Detailed Description, a method for profiling sleep of an individual is provided. The method includes defining a sleep feature space for the individual, measuring a brain wave for the individual during the individual's sleep, and mapping the sleep feature space in response to a comparison of the brain wave and a previous brain wave measurement used to define the sleep feature space. The brain wave may comprise a brain wave spectrum. The sleep feature space may comprise, or be composed of, spectral power and envelope features. The method also includes modelling the mapped sleep feature space in response to recognized neural network patterns corresponding to each of a plurality of sleep stages derived from recognizing the neural network patterns from the sleep feature space and deriving a sleep profile for the individual from sleep stages determined in response to the modelled mapped sleep feature space and the brain wave of the individual.

In addition, a method for modelling sleep profiles for an individual is provided. The method includes measuring a brain wave for the individual and extracting a predetermined number of spectral power ratios of the brain wave. The method also includes processing the predetermined number of spectral power ratios to extract spectral envelope features of the brain wave and extracting Gaussian parameters of the brain wave to form a sleep feature space for profiling sleep of the individual.

In accordance with the Detailed Description, a method for profiling sleep of an individual is provided. The method includes defining a sleep feature space for the individual, measuring a brain wave for the individual during the individual's sleep and generating a second sleep feature space representative of the measured brain wave, and mapping the second sleep feature space to the first sleep feature space by comparing the brain wave and a previous brain wave measurement used to define the first sleep feature space. The brain wave may comprise a brain wave. The sleep feature space may comprise, or be composed of, spectral power and envelope measures. The sleep feature space composed of spectral power and envelope features for the individual is a first sleep feature space. The mapped sleep space and/or the further sleep feature space is a second sleep feature space. The method also includes modelling the first sleep feature space using recognized neural network patterns corresponding to each of a plurality of sleep stages and deriving a sleep profile for the individual from sleep stages by applying the modelled sleep feature space to the mapped sleep feature space.

In accordance with the Detailed Description, a method for profiling sleep of an individual is provided. The method includes defining a sleep feature space for the individual, measuring a brain wave for the individual during the individual's sleep, and mapping features of a further sleep feature space acquired from the brain wave measurement to the spectral power and envelope features. The brain wave may comprise a brain wave spectrum. The sleep feature space may comprise, or be composed of, spectral power and envelope measures. The method also includes modelling the mapped sleep features in response to recognized neural network patterns corresponding to each of a plurality of sleep stages derived from recognizing the neural network patterns from the sleep feature space and deriving a sleep profile for the individual from sleep stages determined in response to the modelled mapped sleep feature space and the brain wave of the individual.

In accordance with the Detailed Description, a method for profiling sleep of an individual is provided. The method includes defining a sleep feature space for the individual, measuring a brain wave for the individual during the individual's sleep, and mapping the sleep feature space in response to a comparison of the brain wave and a previous brain wave measurement used to define the sleep feature space. The brain wave may comprise a brain wave. The sleep feature space may comprise, or be composed of, spectral power and envelope measures. The method also includes modelling the mapped sleep feature space in response to recognized neural network patterns corresponding to each of a plurality of sleep stages derived from recognizing the neural network patterns from the sleep feature space and deriving a sleep profile for the individual from sleep stages determined in response to the modelled mapped sleep feature space and the brain wave of the individual.

BRIEF DESCRIPTION OF DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment.

Skilled artisans will appreciate that elements in the figures are illustrated for simplicity and clarity and have not necessarily been depicted to scale. For example, the dimensions of some of the elements in the illustrations, block diagrams or flowcharts may be exaggerated in respect to other elements to help to improve understanding of the present embodiments.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. Herein, a method for profiling sleep of an individual is presented in accordance with present embodiments having the advantages of more intuitive and information enriched sleep profiling presentation, which is important for home-based sleep monitoring.

Figure 2A:
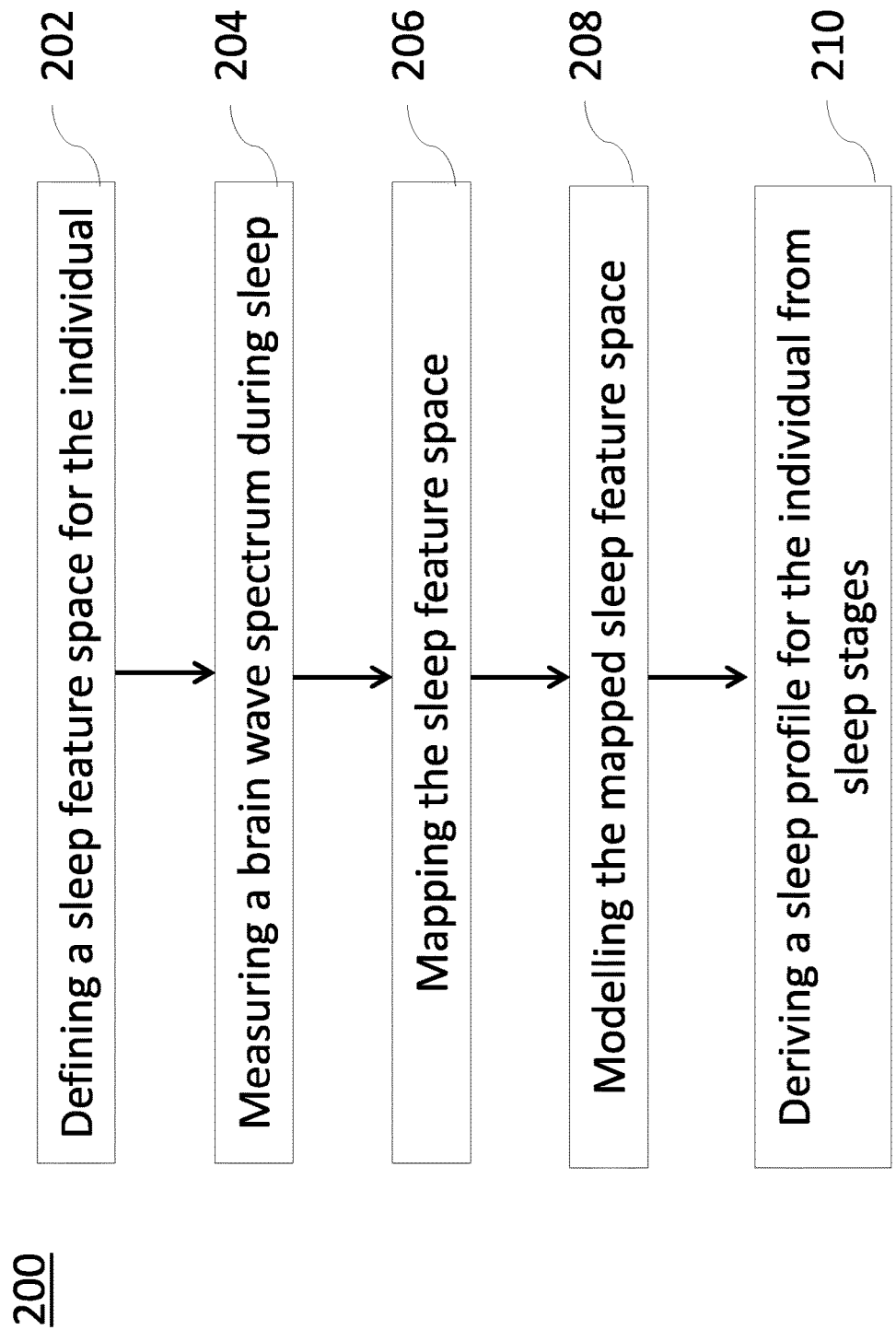
FIGS. 2A and 2B depict examples of flowcharts for methods for profiling sleep in accordance with the present disclosure.

FIG. 2A shows a flow chart illustrating a method 200 for profiling sleep of an individual, according to an embodiment of the invention. The method 200 may be performed by a computer that is coupled to one or more databases. The method may involve communication between devices, such as an EEG taken using an EEG device such as an EEG monitor, headband or cap, connected with a computing device and database in which measurements taken by the EEG device are stored. Communication between the computing device, database and EEG device may be performed using hardwired components, or wirelessly.

The method 200 broadly comprises:

Step 202: defining a sleep feature space for the individual;

Step 204: measuring a brain wave spectrum for the individual during the individual's sleep;

Step 206: mapping the sleep feature space in response to a comparison of the brain wave spectrum and a previous brain wave spectrum measurement used to define the sleep feature space;

Step 208: modelling the mapped sleep feature space in response to recognized neural network patterns corresponding to each of a plurality of sleep stages derived from recognizing the neural network patterns from the sleep feature space; and Step 210: deriving a sleep profile for the individual from sleep stages determined in response to the modelled mapped sleep feature space and the brain wave spectrum of the individual.

Figure 2B:
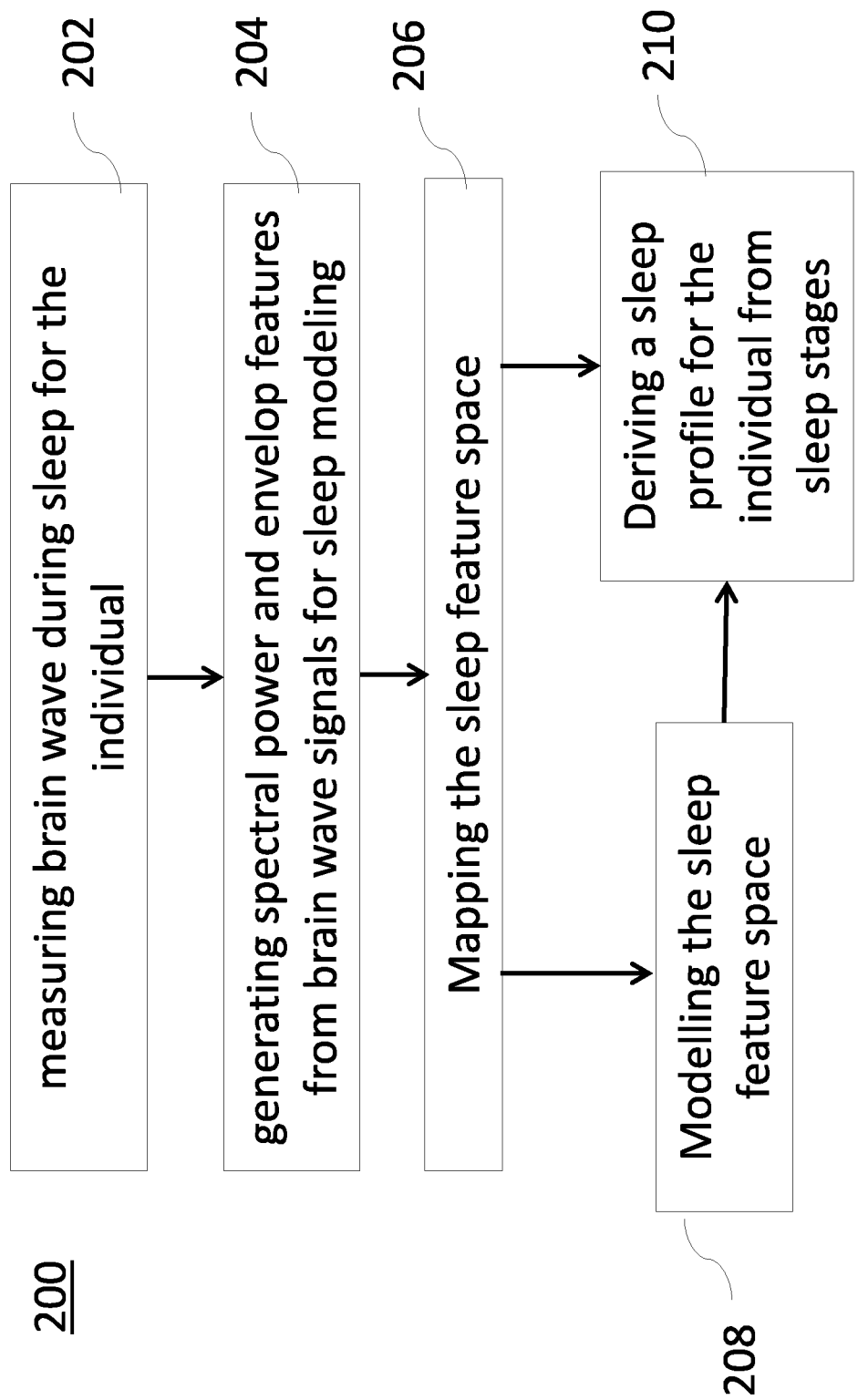

FIG. 2B shows a flow chart illustrating a method 200 for profiling sleep of an individual, according to an embodiment of the invention. The method 200 may be performed by a computer that is coupled to one or more databases. The method may involve communication between devices, such as an EEG taken using an EEG device such as an EEG monitor, headband or cap, connected with a computing device and database in which measurements taken by the EEG device are stored. Communication between the computing device, database and EEG device may be performed using hardwired components, or wirelessly.

The method 200 broadly comprises:

Step 202: measuring brain wave during sleep for the individual;

Step 204: generating spectral power and envelope features from brain wave signal for sleep modeling;

Step 206: mapping the sleep feature space by adjusting the features acquired from a different setting to the features acquired in the previous measurement that were used for modelling.

Step 208: modelling the mapped sleep feature space in response to recognized neural network patterns corresponding to each of a plurality of sleep stages derived from recognizing the neural network patterns from the sleep feature space; and Step 210: deriving a sleep profile for the individual from sleep stages determined in response to the modelled mapped sleep feature space and the brain wave spectrum of the individual.

Step 202 involves measuring brainwave of the individual. The brainwave spectrum may be measured by taking an EEG of the individual. In one example, the EEG is obtained in sleep lab using cap EEG sensors, as shown in 332 of FIG. 3. In another example, the EEG is obtained using a Head Band EEG sensor during a period of an individual's sleep being profiled, as shown in 302 of FIG. 3.

Step 204 involves generating a sleep feature space based on training data such as cap EEG data which may be obtained prior to sleep to be profiled. In one example, the step is conducted as iStaging Feature Generation. After the brain wave of a patient is monitored, the brainwave profile or data are analysed to identify features. This analysis may involve fitting one or more curves to the brainwave profile or data. Parameters describing the one or more curves, such as amplitude and frequency, are then calculated. While previous EEG data may then make direct use of the amplitude and frequency in order to determine the various sleep stages of an individual, some present methods involve determining derivatives and other parameters that reduce the amplitude and frequency variation between individuals (e.g. normalise the data against amplitude variations). Thus a more uniform sleep profile can be automatically applied across an individual's various periods of sleep, despite variations in sleep and wake brain activity between particular periods. This process is explained in further detail with reference to FIG. 3.

Figure 3:
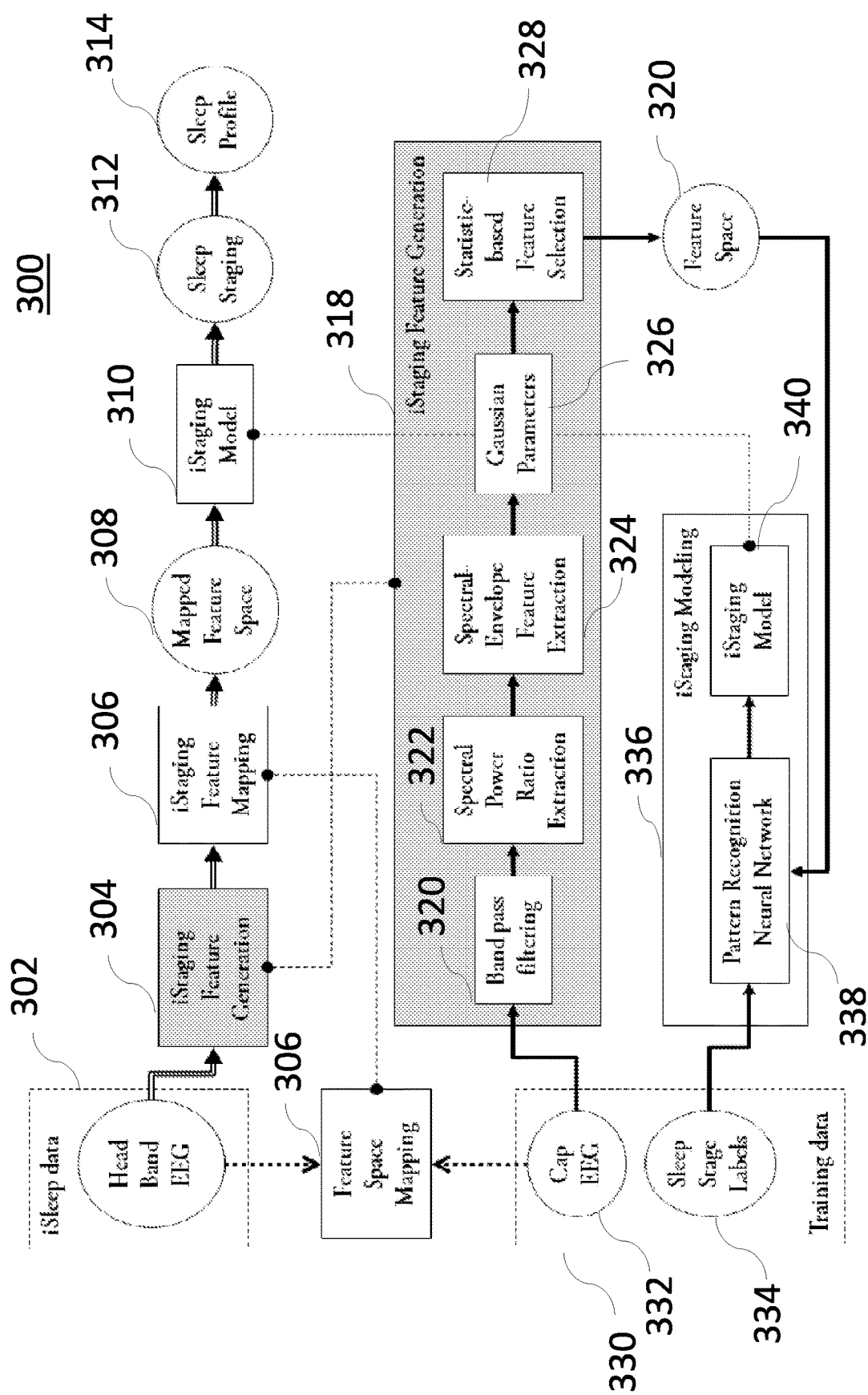
FIG. 3 depicts an example of workflow of the sleep profiling system in accordance with the present disclosure.

Step 206 involves mapping the features extracted from brain wave acquired in different setting into the same feature space. The measured data, for example, from cap EEG, is used for sleep modelling. This mapping may comprise determining which features of the feature space are represented in different portions of the measurements taken in accordance with step 204. This process may also involve generating a sleep feature space representative of the newly measured EEG and comparing the previous sleep feature space to the sleep feature space representative of the newly measured EEG. The mapping may involve mapping the range of features of the previous EEG to the range of features of the new EEG (e.g. by matching the maximum amplitude of the former with that of the latter) or by range matching, in a similar manner, the EEG measurement from which the previous sleep feature space was derived to the newly measured EEG and then generating the sleep feature space for the newly measured EEG. In one example, the mapping is conducted in iStaging Feature Mapping module 306 based on a comparison between Cap EEG data of 332 (i.e. data representing brainwaves measured using an EEG device shaped like a cap) and Head Band EEG data of 302 (i.e. data representing brainwaves measured using an EEG device shaped like a headband) as shown in FIG. 3.

Advantageously, the mapping may be automatically conducted. For example, a computing system may automatically match the amplitudes of features of the respective sleep feature spaces, or of the respective EEG measurements.

Step 208 involves modelling the mapped sleep feature space obtained in step 206. Modelling involves identifying neural network patterns in the sleep feature space based on the new EEG measurement obtained in step 204. This is achieved by identifying those same neural network patterns in the sleep feature space defined in step 202 and step 204 using training data from cap EEG, and identifying similar feature patterns in the sleep feature space obtained in step 202 and step 204 using data from Head band EEG. The similar feature patterns in the sleep feature space obtained in step 202 and step 204 using data from Head band EEG may be identified by probabilistically associating particular groups of features in the sleep feature space obtained in step 202 and step 204 with those in the sleep feature space obtained in step 202 and step 204 that have already been associated with respective recognised neural network patterns indicative of various sleep stages using cap EEG. A particular neural network pattern is then deemed to apply to each respective group of features in the sleep feature space of step 202 and step 204 using data of Head band EEG, depending on the features in the sleep feature space of step 202 and step 204 with which each respective group has the highest probabilistic association. In one example, the step is conducted in the iStaging Modeling module 336 explained with reference to FIG. 3. As shown in FIG. 3, the mapped Feature space 308 forms the basis for the sleep staging process conducted in iStaging Model module 310. The sleep staging process results in the epochs of the EEG forming the basis for the sleep feature space of Step 202 and Step 204 using data of Head band EEG being able to be categorised into four stages, such as Wake, Deep, Light and REM sleep.

Figure 1:
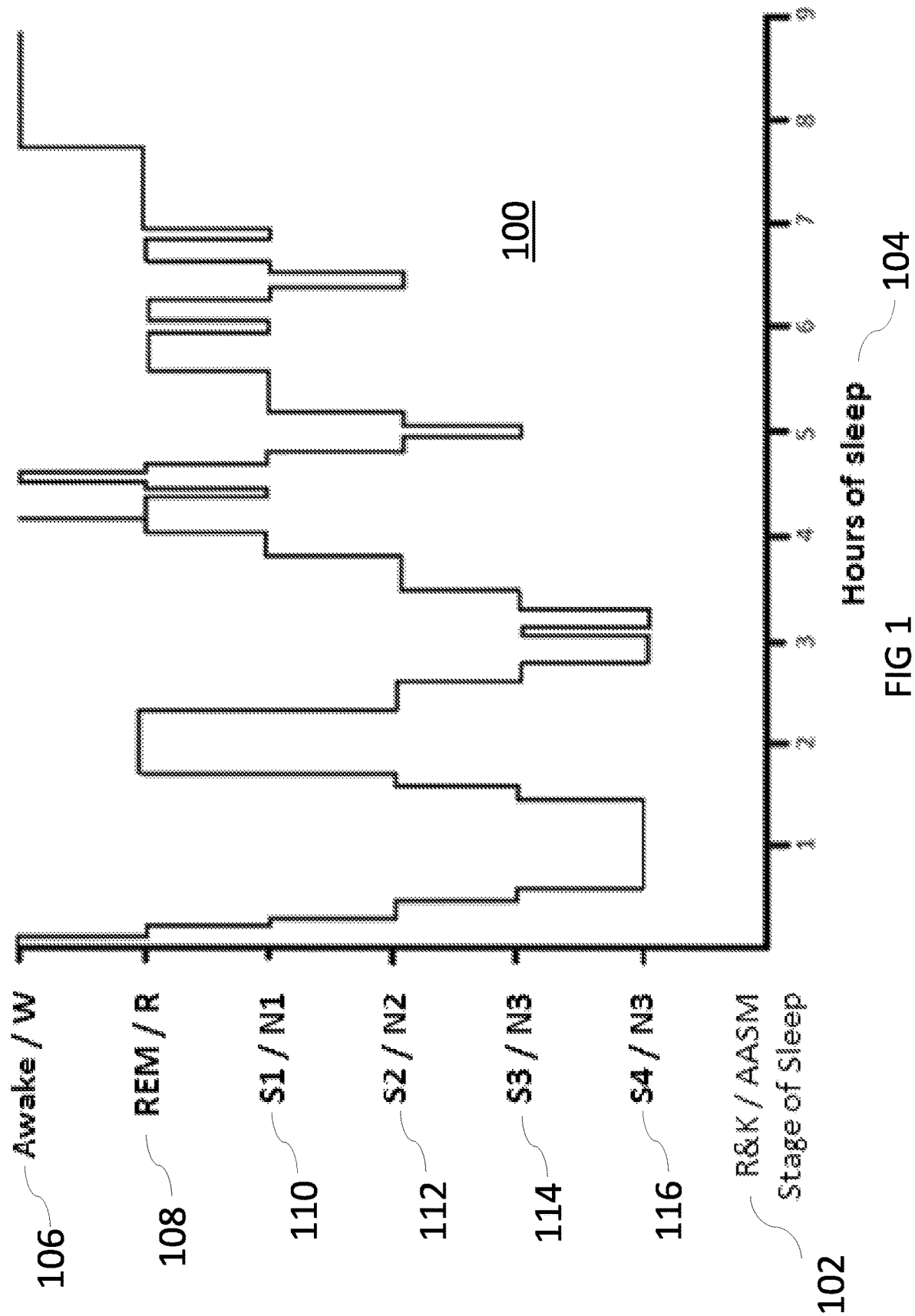
FIG. 1 depicts an example of hypnogram showing the sleep stages in a sleep cycle.

Step 210 involves deriving a sleep profile for the EEG measured in step 204. The sleep profile thus provides a pictorial representation of the change in sleep stage for an individual over the period for which the EEG of step 204 was measured—refer to FIG. 1. Thus the process results in the conversion of new EEG measurements to a sleep profile, based on a previous sleep feature space and known neural network patterns. Experimental data showing validity of the model and sleep profile obtained by the model is described with reference to FIG. 6 and FIG. 7.

FIG. 3 illustrates the framework of the proposed sleep profiling system in accordance with the present disclosure.

The boxes linked by solid arrows 332, 320, 322, 324, 326, 328, 320, 334, 338, 340 form the process of building the computational model—this process is called "iStaging Feature Generation and iStaging Modeling". The boxes linked by outlined arrows 302, 304, 306, 308, 310, 312, 314 are the sleep profiling process using the iStaging model—in other words, the use of the model developed using the iStaging Feature Generation and iStaging Modeling procedure to a new EEG measurement.

Initially, the individual's sleeping patterns should be modelled so that the modelled sleeping patterns can be compared to new sleeping patterns for which no model is readily able to be generated—for example, a sleeping pattern for a period of sleep occurring in-home, without professional assistance. The process of building the computational model herein referred to as iStaging, and is explained with reference to modules of 332, 320, 322, 324, 326, 328, 320, 334, 338 and 340. Preferably, iStaging involves iStaging Feature generation 318 and iStaging modeling 336, which are conducted prior to obtaining a new EEG measurement 302 such as a Headband EEG signal during a period of sleep—herein referred to as iSleep data.

In module 332, training data such as Cap EEG data is obtained using a Cap EEG sensor. This training data is used to develop a sleep feature space that can be compared to sleep feature spaces generated using further EEG measurements that are taken at future dates, for example in the home. The obtained data is used in iStaging Feature Generation 318 and Feature Space Mapping 306. The obtained data is processed with a band-pass filter to remove artefacts, in Band pass filtering module 320. The artefacts may include unusual or unexpected spikes in data readings and periods during which no reading is available (e.g. when the headband becomes dislodged or otherwise ceases to function). With further reference to FIG. 3 and, in particular, band pass filtering module 320, various types of band pass filter may be employed. For example, from PSG data containing whole night EEG with sleep stage annotation 332 (e.g. by a sleep specialist), raw EEG of bipolar (FPz-Cz) (FPz stands for Prefrontal zone and Cz stands for Central zone) signal is first processed with a Butterworth band-pass filter to remove artefacts resulting from occasional poorly contacted EEG electrodes in module 320. The cut-off frequency is set to {0.35-48} Hz, upper bounded by the sampling rate.

Thereafter, the spectral band power features of the filtered data are extracted in Spectral Power Rate Extraction module 322. For robust and subject-independent quantity measurement of the spectrum power, the energy power ratio instead of absolute energy power is calculated. Using the energy power ratio increases the standardisation or normalisation of the data, for example, with respect to amplitude. This can account for daily variations in brain activity of an individual and ensure that neural network patterns identifiable by such ratios in one sleep feature space can be comparably identified in other sleep feature spaces as a result of data not being obscured by external factors such as fatigue and age.

For example, it is known that EEG properties, particularly amplitude, vary among different subjects. Energy power ratio is calculated instead of absolute energy power in order to produce robust and subject-independent quantity measurements of the spectrum power in module 322. Temporal shifting windows of 2s with 50% overlap are used to compare consecutive temporal segments, which represent data of current instance of time under analysis, with relation to past and future data. The spectral features are extracted along the 2s shifting window using fast Fourier transformation (FFT). The total power spectrum is calculated by summing up the power spectrum among the cut-off frequency bands:

$$P_{total} = \sum_{f=F_{min}}^{F_{max}} P(f)$$

Where $P(f)$ is the power of frequency f, with $F_{max}$=48 Hz and $F_{min}$=0.35 Hz. The power ratio of each frequency band is defined as:

$$Pr(i) = \frac{\sum_{f=f_{low}(i)}^{f_{high}(i)} P(i)}{P_{total}}$$

Where $f_{low}(i)$ and $f_{high}(i)$ indicate the range of the respective spectral power band. The boundaries are represented as an vector of frequency bands B={0.35 2 4 8 12 16 24 48}, from which any band pass definition can be obtained, e.g. the $f_{low}(2)$=2 Hz and $f_{high}(2)$=4 Hz. The vector B was chosen after many rounds of experiments for the optimal setting, which well matches the bands that plays important roles in different sleep stages, e.g., Delta(0.5-4 Hz), Spindle (12-16 Hz), Beta(12-30 Hz), Alpha (8-12 Hz) etc, as described in table 1.

TABLE 1

Characteristics of EEG signals in difference sleep stages

| Stage | Characteristics of EEG signals |
|---|---|
| Wake | Beta (12-30 Hz), Alpha (8-12 Hz) |
| N1 | Alpha, Theta(4-8 Hz) |
| N2 | Alpha, Theta, K-complex, spindle waves |
| N3 | Delta (0.5-4 Hz), Spindle (12-16 Hz) |
| REM | Delta |

This step yields 7 spectral power ratios Pr={pr(i)}; i=1 . . . 7 that are further processed by spectral envelope feature extraction in module 324.

In module 324, a spectral envelope is generated. The spectral envelope defines the magnitude of the spectral power ratios (e.g. the spectral power ratios determined over successive periods of time) obtained in module 322. After forming the spectral envelope, spectral envelope features are extracted that define the spectral envelope. The spectral envelope features make evident the periodic nature of a categorical time series and, in the present case, of the variation in spectral power ratio over time as extracted in module 322.

The concept of a spectral envelope for spectral analysis has been used in automatic speech recognition (ASR). Such a feature serves as an efficient tool for exploring the periodic nature of a categorical time series with minimum loss of information. A feature extraction method is introduced herein with envelope-based spectral filtering, aimed at suppressing the color noise appearing in a spectral power periodogram. The pass band and stop band edge frequencies are created for a Chebyshev filter, a specially defined spectral space of {0-0.5} Hz being further divided into 2 bands in a log-space. Chebyshev type II filter is applied to the 7 spectral power bands acquired as discussed above, yielding another 14 parameters for spectral analysis.

Thereafter, the spectral power ratios are modelled using a Gaussian distribution and parameters of the Gaussian distribution are extracted to form the sleep feature space in module 326 for successive windows or epochs over the EEG. For example, the mean and deviations (e.g. standard deviations) of the parameters are extracted.

The standard sleep staging window size is 30 seconds according to AASM scoring. There are 21 parameters able to be extracted along a 2 second shifting window exhibited in the Gaussian distribution each the 30 second window in module 326. The mean and variations of the parameters are extracted to form a feature space having 42 features in module 328. In comparison to the established feature set which has been previously developed for EEG based sleep stage detection, the spectral envelope-based features, comprised of spectral powers and their spectral derivatives, form a better representative feature space 320.

Module 328 then statistically selects particular features to form the sleep feature space. This statistical selection may involve weighting particular features depending on their relative importance in defining the particular sleep stage to which the relevant spectral power ratios apply (e.g. by recognising neural network patterns in the portion of the EEG from which the respective spectral power ratios were derived). Alternatively, or in addition, statistical selection may involve identifying features that appear more regularly, or with greater amplitude, during a particular sleep stage when compared with other features.

This statistical analysis results in the creation of sleep feature space 320 comprising, for example, vectors each of which represents a particular sleep stage and against which sleep feature spaces of future EEGs can be compared to determine the statistically highest probability sleep stage for each epoch in the respective future EEG. This is further explained with reference to Table 2 and FIG. 6.

After generating sleep feature space 320, the computational model is built in sleep feature modelling module 336. In module 338, neural network patterns are identified in the training data (i.e. the data from which the sleep feature space of step 202 was derived). During the initial modelling process, the system must be trained to recognise particular neural network patterns in EEG data (i.e. to identify particular sleep stages). This may be achieved by inputting the EEG data used as the basis for the iStaging Feature Generation process, after annotation by, for example, a sleep specialist. Thus module 338 can associate particular sleep stages with particular EEG features, that are then associated with groups of features in the sleep feature space. Those groups of features can then be compared to similar features derived from new EEG measurements. The model produced in the iStaging Model module 340 thus associates different sleep stages with features represented in the sleep feature space, and can be used for subsequent sleep profiling. Details of sleep feature model is described with reference to FIG. 4.

Once modelled, the model can be applied to new EEG measurements to profile an individual's sleeping patterns. The sleep profiling process uses the sleep staging model explained with reference to modules 302, 304, 306, 308, 310, 312 and 314. In module 302, a brain wave spectrum is measured using sensor such as Head Band EEG sensor. The collected data is provided to sleep feature generation module 304 and sleep feature mapping module 306. Notably, while the model may be generated using a cap EEG device (i.e. a highly sensitive EEG device) the EEG device used in-home may have lower sensitivity or have greater noise on the reading, since features extracted from any EEG measured using the in-home device are weighted against features that are important for determining particular sleep stages.

In module 304, sleep feature space is generated in the same manner as described above with reference to module 318. Since the readings from one EEG sensor may differ to those obtain through another EEG sensor for the same brain activity, previous processes have suffered from a transfer learning problem—the conclusions learned using one device applied to one EEG signal cannot readily be transferred to other devices. In the present case, sleep feature mapping module 306 is inserted after sleep feature generation module 304. In sleep feature mapping module 306, automatic feature mapping is conducted so that sleep data such as the signal obtained in module 302 is mapped to training data such as Cap EEG data determined by module 332 for use in sleep feature generation. As discussed above, the mapping may result, for example, from normalisation or amplitude matching in EEG measurements.

Mapped feature space 308 generated in sleep feature mapping module 306 is used in sleep feature model module 310. In this round, since the EEG device has already been taught which sleep stages correspond to which features apparent in an EEG measurement, the previously developed model can be applied without sleep professional intervention, in order to automatically determine the particular sleep stages of an individual. This determination may be made in real-time since the complicated processing used to produce the model has already taken place. Moreover, the process of applying the model may involve only the calculation of probabilities based on the features known to describe particular sleep stages.

Once the model is applied to the mapped feature space 308 each epoch of the EEG, as represented by the mapped feature space 308, is associated with a particular sleep stage 312. Based on sleep stage 312 produced in sleep feature model module 310, a sleep profile 314 is produced. The sleep profile 314 pictorially represents the sleep stage of the individual over the recording period of the EEG Thus, a more intuitive and informative sleep profiling presentation is achieved in this sleep profiling process. Moreover, since the modelling and profiling can be conducted in real-time, problematic sleep disorders and the like can be diagnosed and responded to in a shorter period than has heretofore been readily available in an in-home context.

Automatic sleep stage detection is a multi-class classification problem. A multi-layered pattern recognition neural network is developed to model the problem. The network comprises an input layer mapped onto iStaging feature space, one 10 nodes hidden layer map the input space to an output layer, and a output layer with each of the plurality of output nodes associated with a sleep stage. Pattern recognition networks such as that developed at 338, in module 336, can be trained by backpropagation manner to classify inputs according to target classes. The target data for the networks may consist of vectors of all zero values except for a 1 in element s, where s is the sleep stage. The input to the network is the feature space 320 representing the Gaussian distribution of the power spectrum and their envelope features, obtained in sleep feature generation module 318. A further input may be the EEG annotated by a sleep specialist.

Figure 4:
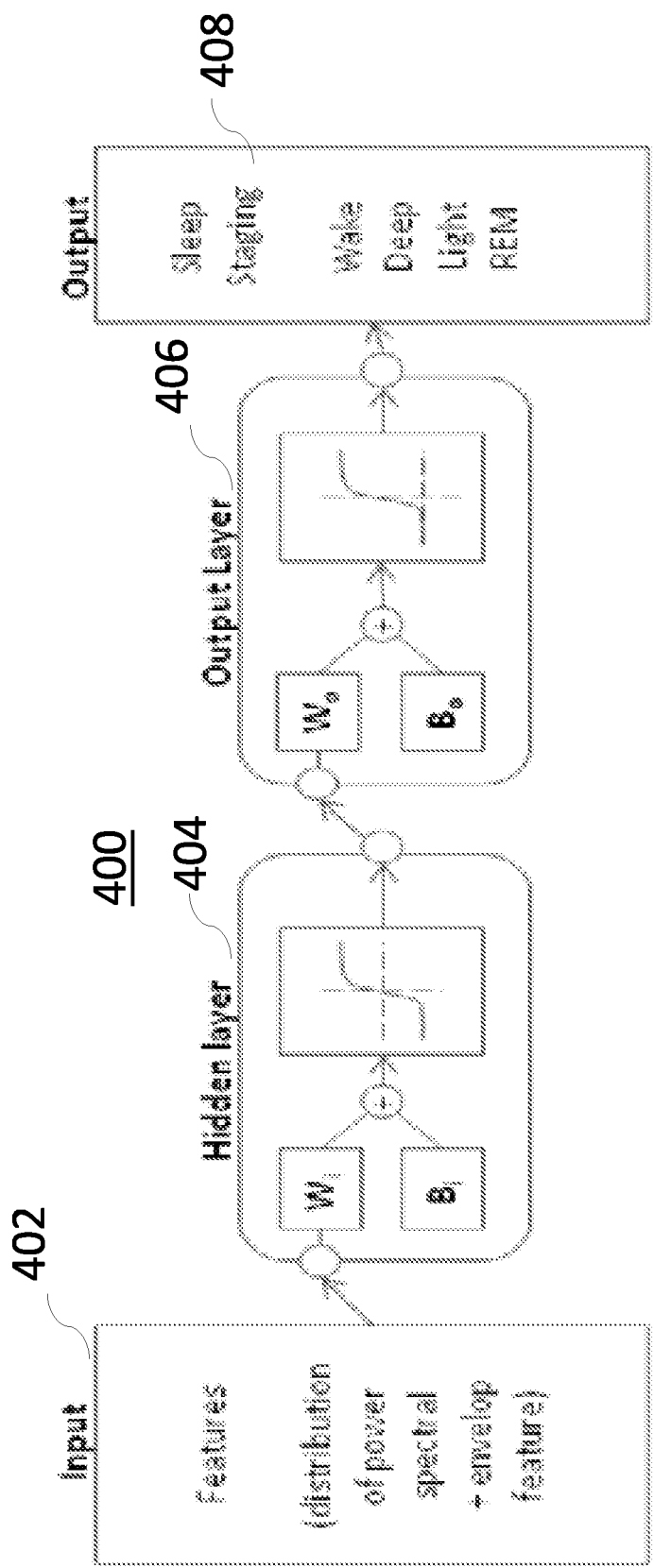
FIG. 4 depicts an example of Pattern recognition neural network for sleep stage prediction in accordance with the present disclosure.

FIG. 4 shows an embodiment of such a sleep stage pattern recognition network 400. The pattern recognition neural network learned used the defined input 402 and output 408 is the iStaging model 336 which can be further used for sleep stage detection 312 in future EEG.

The iStaging model 340, 310 contains parameters of the weight matrix and bias vectors for hidden layer 404 and output layer 406 ($W_i, B_i, W_o, B_o$), which are used to infer a sleep stage from the input features 402. The calculation of sleep stage can be realized by the following:

Output=log sig($W_o$*(tan sig($W_i$*Input+$B_i$)+$B_o$)

These weightings are used to emphasis particular features in a sleep feature space, over other features, where the emphasised features provide a greater statistical certainty than the other features that the relevant epoch is one during which the individual is in a particular sleep stage.

The transfer functions used in the pattern recognition network may be the log-sigmoid (logistic) and tan-sigmoid, which are given by:

$$\text{logsin}(x) = \frac{1}{1+e^{-x}} \text{ and } \text{tansin}(x) = \frac{2}{1+e^{-2x}} - 1,$$

the output may be a vector containing 4 values, with each representing the posterior probability of sleep stage s.

Applying the iStaging model 340 learned from cap EEG sensor 332 to a new scenario (i.e. a new EEG measurement) where signals are acquired from a new EEG sensor is a transfer learning problem as discussed above. To address the problem, the previously proposed feature range mapping method is provided that automatically maps the new signals to the signals used in iStaging model development in module 306. A simple implementation of the mapping can be to align the feature space extracted from headband EEG to the range of the respective feature space that is extracted from cap EEG.

A sleep hyponogram as a tool for professionals to analyse sleep patterns gives less-intuitive information for a lay person to understand his or her sleep profile. Hence a more intuitive and information rich sleep profiling presentation such as that presently presented is important for home-based sleep monitoring.

Figure 5:
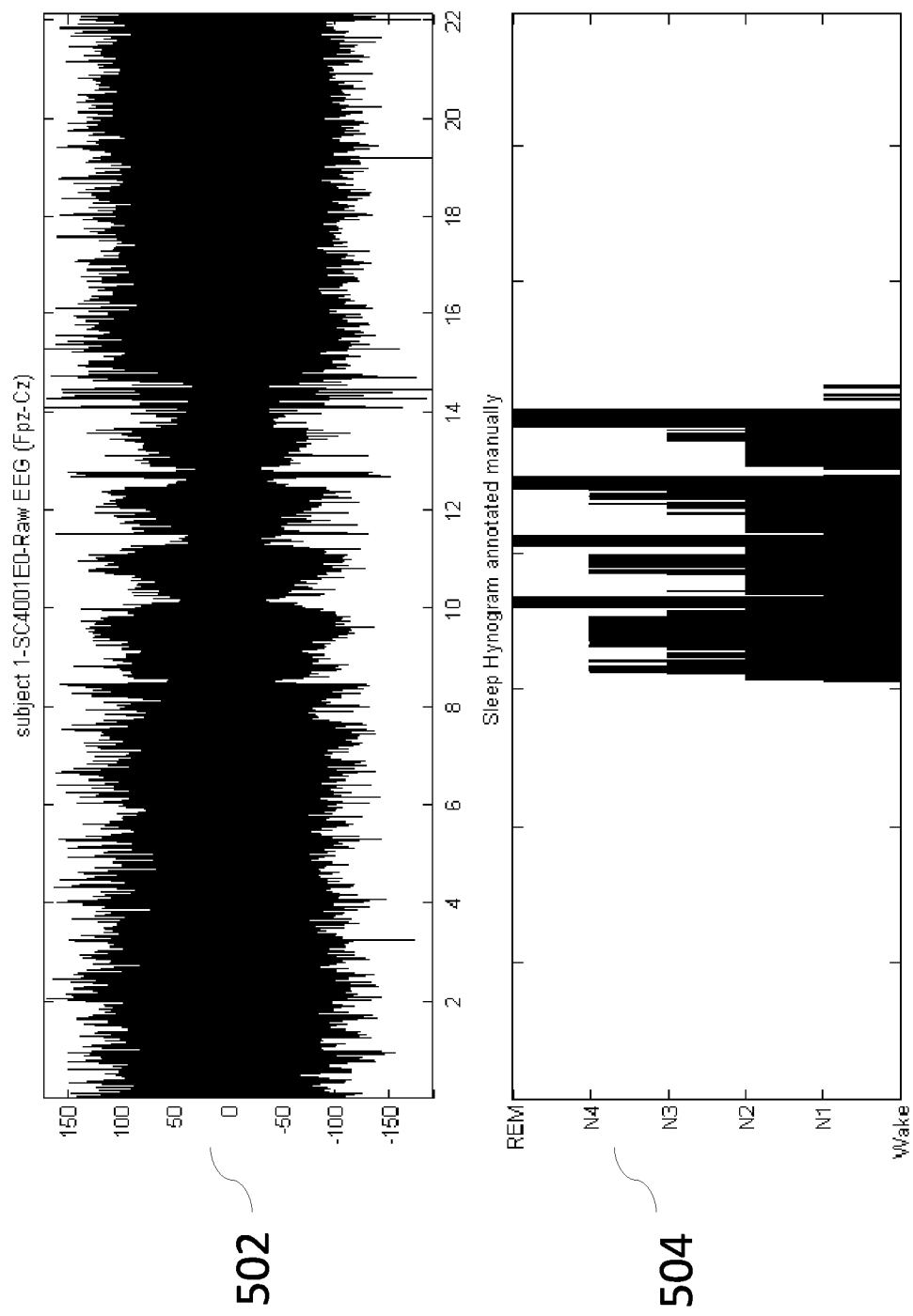
FIG. 5 depicts an example of EEG signals and manually marked sleep stages from a subject.

EEG data that is recorded all night is obtained and compared to corresponding sleep stage labelling from an established and publicly available database. The database has a collection of 61 PSGs with accompanying hypnograms coming from two separate studies. The whole-night PSG sleep recordings contain bi-polar EEG signal (Fpz-Cz and Pz-Oz), (Fpz stands for Prefrontal zone, Cz stands for Central zone, Pz stands for Parietal zone and Oz stands for Occipital zone) EOG (horizontal) and EMG (chin) readings. The hypnograms contain annotations of the sleep patterns that correspond to the PSGs, consisting of sleep stages W, R, 1, 2, 3, 4, M (Movement time) and ? (not scored). All hypnograms in the database have been manually scored by well-trained technicians. The PSG files are formatted in European Data Format (EDF) while the hypnograms are in EDF+. Fpz-Cz EEG signals are extracted and the corresponding Sleep Stages from the source files to form the ground truth data for modelling. Data from subjects with sleep stage W missing is removed, as only night EEG are recorded for them. There are 39 subjects who had both their day-time and night-time EEG recorded where all sleep stages are available. To further cleanup the data, all segments of stage M (movement) or ? (not scored) can be removed. FIG. 5 shows a sample dataset plotting EEG signal 502 and sleep stage of one subject 504. To simplify the model, stages S1 and, S2 are combined into a 'light sleep' stage and stages S3 and S4 are combined into a 'deep sleep' stage to differentiate the discriminative power of each feature between the sleep stages.

Table 2 describes the features that are extracted from Pfz-Cz bi-polar EEG signal using the method described in iStaging Feature Generation 318 of FIG. 3. The first set of 21 features are the means and last set of 21 features are the standard deviations of filter band power and their respective envelope features.

TABLE 2

Feature list (before feature selection)

| Features | Description of features |
|---|---|
| 1-7 | mean band power ratio of the 7 bands in 30 sec |
| 8-14 | mean lower band spectral envelop feature of the 7 bands in 30 sec |
| 15-21 | mean higher band spectral envelop feature of the 7 bands in 30 sec |
| 22-28 | Standard deviation of the band power ratio of the 7 bands in 30 sec |
| 29-35 | Standard deviation of the lower band spectral envelop feature of 7 bands in 30 sec |
| 36-42 | Standard deviation of the higher band spectral envelop feature of the 7 bands in 30 sec |

Figure 6:
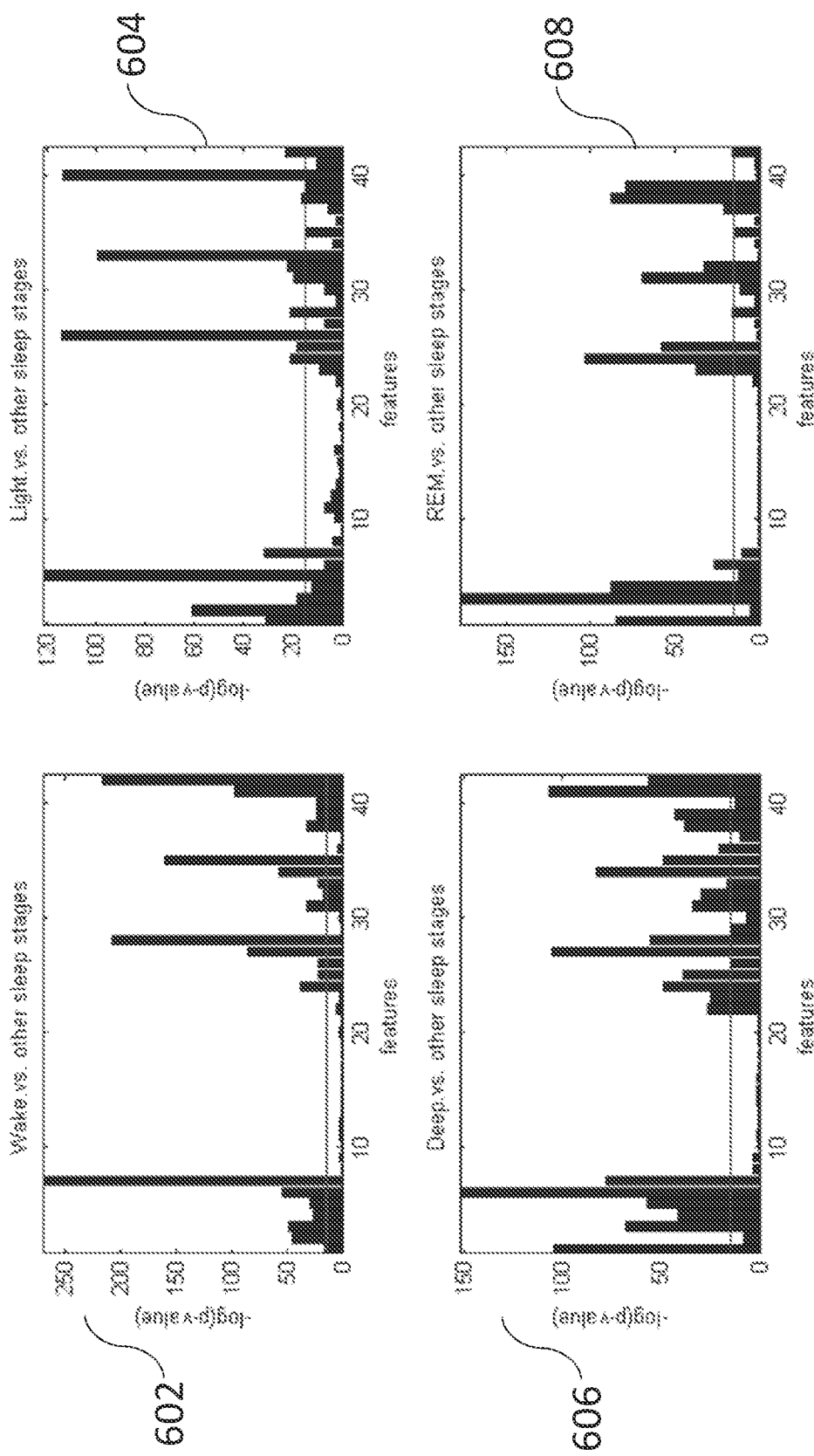
FIG. 6 depicts an example of statistic test for features in accordance with the present disclosure. Y-axis stands for −log(p-value). X-axis stands for 42 features extracted from EEG signal. The line parallel to X-axis stands for the threshold where statistical difference found between two groups.

To illustrate the discriminative power of each feature, two-sample T-Tests for four groups of samples are conducted, i.e.:

Wake vs. other stages 602,
light sleep vs. other stages 604,
Deep sleep vs. other stages 606, and
REM vs. other stages 608, as shown in FIG. 6. The large sample size from the 30 second segments in 24 hour periods incur a multiple comparison problem. The p-value (Alpha) of the T-Test can be adjusted with Bonferroni correction, e.g., $$\alpha^* = \frac{\alpha}{C_2^N}$$

where N is the size of test, $\alpha=0.05$, and $\alpha^*$ is the adjusted threshold for statistical significance.

FIG. 6 shows the significance level of each feature in 4 groups of statistic tests. The y-axis is $-\log(p\text{value})$, thus the higher the bar, the lower the p-value and the more useful the feature is in separating the two groups of samples. The horizontal line is the statistical significance threshold adjusted by Bonferroni correction, i.e., $-\log(\alpha^*)$. Features 1-7, mean band power ratio, are often the most important features. Features 22-42, the standard deviation of band power ratio and envelope features, follow in relevancy and also demonstrate strong discriminative power. However, features 8-21, the mean of respective envelopes features, display no discriminative power in all four tests and may thus be removed from the feature space. The final feature space hence contains 28 features.

Figure 7:
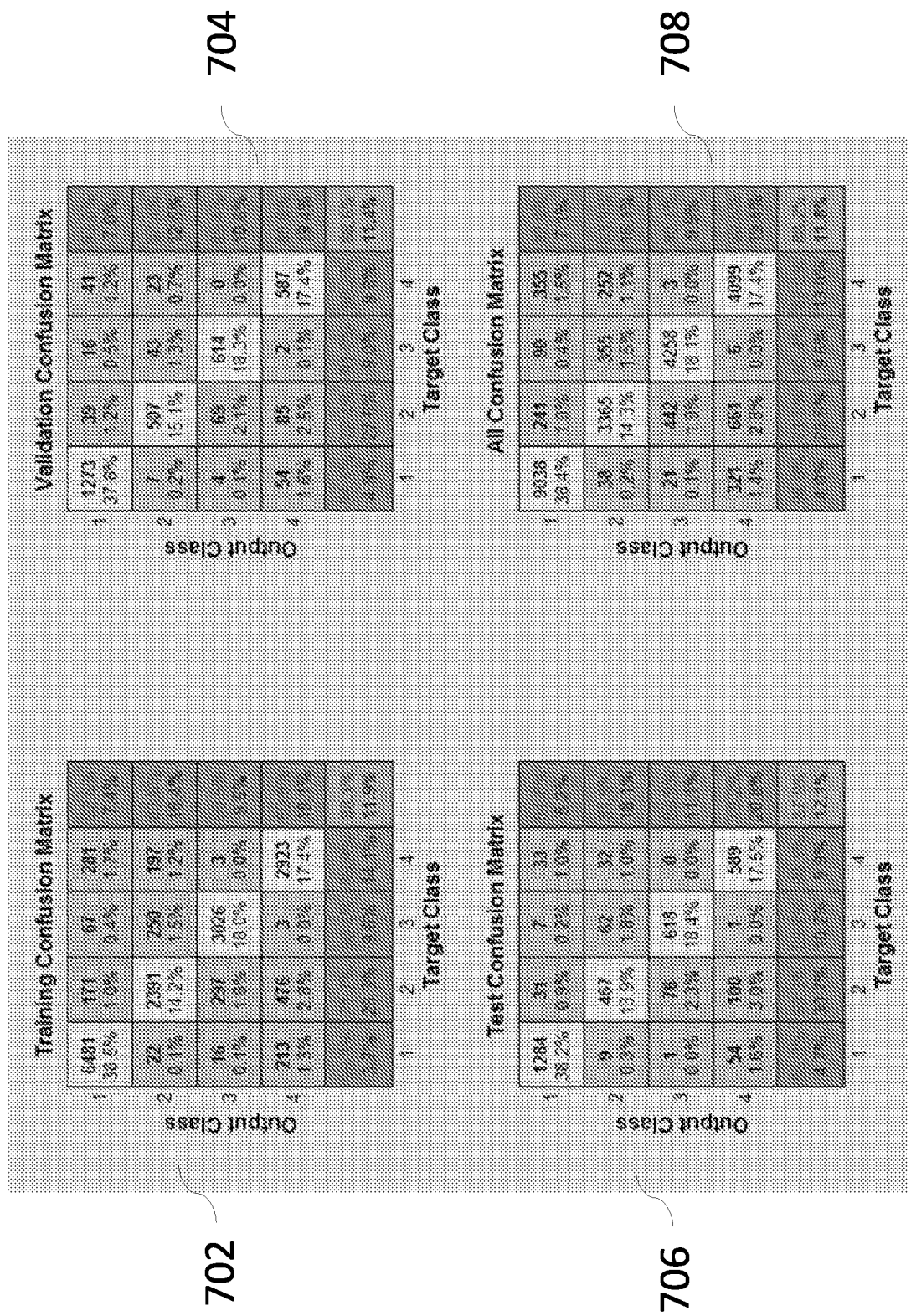
FIG. 7 depicts an example of confusion tables for Training, validation, and testing in Pattern recognition network in accordance with the present embodiment.

To validate the usefulness of the iStaging model, leave-one-out cross validation is conducted on the 39 subjects that have 24 hour EEG data. For each of the 39 subjects, models using data from all the other subjects are built and tested on the one left out. The 3-layer pattern recognition network is defined to have 10 hidden nodes with 70% data for training 702, 15% data for validation 704 and 15% for testing 706. FIG. 7 shows the result of building the model using data from one of the subject. The confusion matrix of various data sets gives the accuracy of sleep stage prediction, where 1 represents the awake stage, 2 represents the light sleep stage, 3 represents the deep sleep stage and 4 represents the REM stage.

The sensitivity and specificity for each sleep stage are calculated, and the overall accuracy for all stages determined. For stage s, the sensitivity and specificity for sleep stage S is defined as:

$$\text{Sensitivity} = \frac{TP_s}{TP_s + FN_s}, \text{Specificity} = \frac{TN_s}{TN_s + FP_s}$$

where $TP_s$ and $FN_s$ denotes the number of true positives and false negatives for sleep stage S detection, and $TN_s$ and $FP_s$ denotes the number of true negatives and false positives for sleep stage S detection. The overall accuracy is:

$$\text{Accuracy} = \frac{1}{s} \sum_{s=1}^{4} \frac{TP_s + TN_s}{TP_s + TN_s + FP_s + FN_s}$$

In the results of all 39 leave-one-out cross validation test, the average overall test accuracy is 85.5%. The average sensitivity of light sleep is only 69.5%, which is the main factor affecting the overall accuracy. The most accurately detected sleep stage is the awake stage, where both sensitivity and specificity are higher than 94%.

The object of building the iStaging model is to use it for automatic sleep stage detection in a light weight headband EEG system. Therefore, the model needs to be adapted for EEG data collected from a headband sensor 302. As mentioned in the preceding paragraphs, there is a transfer learning problem inherent in porting models derived from a sensitive and accurate apparatus, employed under controlled laboratory conditions by a sleep specialist, to an in-home, less accurate and potentially misused device. This issue can be addressed by the iStaging Mapping method conducted in module 306. EEG data is collected for 1-hour naps in experiments conducted. The result is highly agreeable with the sleepiness score obtained. As the experiments were conducted during daytime where subjects took 1-hour naps, no deep sleep stages occurred. Spectral features of REM stages showed similar characteristics as those of the light sleep stages, so there exists mis-detection of light sleep as REM, which can be corrected using smoothing methods with consideration given to sleep architecture.

In conclusion, a feature generation and feature mapping mechanism for sleep profiling and a system thereof have been provided. In addition, a method for highly accurate sleep stage detection based on Gaussian distribution of power spectral and envelop-based features is also provided. A method for automatic real-time feature mapping using a EEG sensor and a method to produce sleep profile based on EEG-based sleep staging are also provided.

While exemplary embodiments have been presented in the foregoing detailed description of the invention, it should be appreciated that a vast number of variations exist.

It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of elements and method of operation described in an exemplary embodiment without departing from the scope of the invention as set forth in the appended claims.

What is claimed is:

1. A method for determining one or more sleep disorders of an individual, the method comprising:
    measuring a first brain wave of the individual during the individual's sleep;
    extracting a predetermined number of spectral power ratios of the first brain wave;
    processing the predetermined number of spectral power ratios to extract spectral envelope features of the first brain wave;
    extracting Gaussian parameters of the first brain wave to define a sleep feature space for profiling sleep of the individual;
    measuring a second brain wave for the individual during the individual's sleep;
    mapping the sleep feature space in response to a comparison of the second brain wave measurement to the first brain wave measurement used to define the sleep feature space;
    modelling the mapped sleep feature space in response to recognized neural network patterns corresponding to each of a plurality of sleep stages derived from recognizing the neural network patterns from the sleep feature space;
    deriving a sleep profile for the individual from sleep stages determined in response to the modelled mapped sleep feature space and the second brain wave of the individual; and
    determining the one or more sleep disorders of the individual from the sleep profile,
    wherein extracting each of the predetermined number of spectral power ratios of the first brain wave comprises:
        identifying a plurality of temporally shifted overlapping spectrum windows from the first brain wave;
        extracting special features of the plurality of temporally shifted overlapping spectrum windows;
        determining a total power for a predetermined number of cutoff frequency bands within the first brain wave; and
        determining the predetermined number of spectral power ratios of the first brain wave based on the total power and a spectral band power for each of the predetermined number of cutoff frequency bands.

2. The method in accordance with claim 1, wherein processing the predetermined number of spectral power ratios to extract spectral envelope features of the first brain wave includes envelope-based spectral filtering the predetermined number of spectral power ratios by a Chebyshev type II filter to extract multiple spectral envelope features for each spectral power ratio of the first brain wave.

3. The method in accordance with claim 1, wherein extracting the Gaussian parameters includes extracting a mean and variations of the predetermined number of spectral power ratios of the first brain wave and of the spectral envelope features extracted from the predetermined number of spectral power ratios to define the sleep feature space for profiling sleep of the individual.

4. The method in accordance with claim 1, wherein measuring the first brain wave of the individual during the individual's sleep comprises measuring EEG signals of the individual during the individual's sleep in-home and without professional assistance.

5. A method for determining one or more sleep disorders of an individual, the method comprising:
- defining a first sleep feature space for the individual;
- measuring a brain wave for the individual during the individual's sleep;
- generating a second sleep feature space representative of the brain wave;
- mapping the second sleep feature space to the first sleep feature space by comparing the measured brain wave and a previously measured brain wave used to define the first sleep feature space;
- modelling the first sleep feature space using recognized neural network patterns corresponding to each of a plurality of sleep stages;
- deriving a sleep profile for the individual from sleep stages determined by applying the modelled sleep feature space to the mapped sleep feature space; and
- determining the one or more sleep disorders of the individual from the sleep profile,
- wherein defining the first sleep feature space comprises defining the first sleep feature space in response to extracting a predetermined number of spectral power ratios of the previously measured brain wave, wherein extracting each of the spectral power ratios of the previously measured brain wave comprises:
  - identifying a plurality of temporally shifted overlapping spectrum windows from the previously measured brain wave;
  - extracting spectral features of the plurality of temporally shifted overlapping spectrum windows;
  - determining a total power for a predetermined number of cutoff frequency bands within the previously measured brain wave; and
  - determining the predetermined number of spectral power ratios of the previous measured brain wave based on the total power and a spectral band power for each of the predetermined number of cutoff frequency bands.

6. The method in accordance with claim 5 wherein measuring the brain wave comprises measuring an EEG of the individual during the individual's sleep in-home and without professional assistance.

7. A system for real-time sleep in-home monitoring of an individual to determine or more sleep disorders of the individual comprising:
- an electroencephalogram (EEG) device configured to measure a brain wave of an individual; and
- a computing device configured to define a sleep feature space for profiling sleep of the individual based on a previously measured brain wave by:
  - extracting a predetermined number of spectral power ratios of the previously measured brain wave, wherein extracting each of the predetermined number of spectral power ratios of the previously measured brain wave comprises:
    - identifying a plurality of temporally shifted overlapping spectrum windows from the previously measured brain wave;
    - extracting spectral features of the plurality of temporally shifted overlapping spectrum windows;
    - determining a total power for a predetermined number of cutoff frequency bands within the previously measured brain wave; and
    - determining the predetermined number of spectral power ratios of the previously measured brain wave based on the total power and a spectral band power for each of the predetermined number of cutoff frequency bands;
  - processing the predetermined number of spectral power ratios to extract spectral envelope features of the previously measured brain wave; and
  - extracting Gaussian parameters of the previously measured brain wave to define the sleep feature space for profiling sleep of the individual, and
- wherein the computing device is coupled to the EEG device for receiving a brain wave measured by the EEG device during the individual's sleep in-home, and wherein the computing device is further configured to derive and present a sleep profile of the individual in real-time in-home based on the brain wave measured by the EEG device during the individual's sleep in-home by:
  - mapping the sleep feature space in response to a comparison of the brain wave measured by the EEG device during the individual's sleep in-home to the previously measured brain wave;
  - modelling the mapped sleep feature space in response to recognized neural network patterns corresponding to each of a plurality of sleep stages derived from recognizing the neural network patterns from the sleep feature space; and
  - deriving the sleep profile for the individual from sleep stages determined in response to the modelled mapped sleep feature space and the brain wave of the individual measured by the EEG device during the individual's sleep in-home.

* * * * *